US009629951B2

(12) United States Patent
Delmage et al.

(10) Patent No.: US 9,629,951 B2
(45) Date of Patent: Apr. 25, 2017

(54) MODULAR HEMOFILTRATION APPARATUS WITH REMOVABLE PANELS FOR MULTIPLE AND ALTERNATE BLOOD THERAPY

(71) Applicant: B. BRAUN AVITUM AG, Melsungen (DE)

(72) Inventors: J. Michael Delmage, Napa, CA (US); Harold W. Peters, Martinez, CA (US); Tommy Cooper, Friendswood, TX (US)

(73) Assignee: B. BRAUN AVITUM AG, Melsungen (DE)

( * ) Notice: Subject to any disclaimer, the term of this patent is extended or adjusted under 35 U.S.C. 154(b) by 241 days.

(21) Appl. No.: 14/258,560

(22) Filed: Apr. 22, 2014

(65) Prior Publication Data

US 2014/0224713 A1    Aug. 14, 2014

Related U.S. Application Data

(62) Division of application No. 12/183,527, filed on Jul. 31, 2008, now Pat. No. 8,747,662.

(60) Provisional application No. 60/953,577, filed on Aug. 2, 2007.

(51) Int. Cl.
*A61M 1/34* (2006.01)
*A61M 1/36* (2006.01)
*A61M 1/16* (2006.01)

(52) U.S. Cl.
CPC ............... *A61M 1/34* (2013.01); *A61M 1/36* (2013.01); *A61M 1/3621* (2013.01); *A61M 1/16* (2013.01); *A61M 2205/12* (2013.01); *A61M 2209/084* (2013.01)

(58) Field of Classification Search
CPC  A61M 1/16; A61M 1/34; A61M 1/36; A61M 1/3621; A61M 2205/12; A61M 2209/084
See application file for complete search history.

(56) References Cited

U.S. PATENT DOCUMENTS

| | | |
|---|---|---|
| 5,200,090 A | 4/1993 | Ford et al. |
| 5,437,624 A | 8/1995 | Langley |
| 5,441,636 A | 8/1995 | Chevallet et al. |
| 5,605,627 A | 2/1997 | Carlsen et al. |
| 5,679,245 A | 10/1997 | Manica |
| 5,910,252 A | 6/1999 | Truitt et al. |
| 6,200,485 B1 | 3/2001 | Kitaevich et al. |
| 6,659,973 B2 | 12/2003 | Gorsuch et al. |
| 6,849,183 B2 | 2/2005 | Gorsuch et al. |

(Continued)

OTHER PUBLICATIONS

Akinori Sueoka, "Present Status of Apheresis Technologies, Part 2, Membrane Plasma Practionator," Therapeutic Apheresis, vol. 1, No. 2, May 1997, pp. 135-146.

(Continued)

*Primary Examiner* — Dirk Bass
(74) *Attorney, Agent, or Firm* — RatnerPrestia

(57) ABSTRACT

An apparatus for performing blood therapy having a plurality of pumps for engaging blood and fluid tubing is characterized by a plurality of manually mounted and disengagable panels installed on the sides of the apparatus housing, the panels having pump engaging tubing mounted on the inside of the respective panels.

6 Claims, 11 Drawing Sheets

(56) References Cited

U.S. PATENT DOCUMENTS

| | | | |
|---|---|---|---|
| 7,169,352 B1 * | 1/2007 | Felt | A61M 1/0209 210/645 |
| 7,223,338 B2 | 5/2007 | Duchamp et al. | |
| 7,232,418 B2 | 6/2007 | Neri et al. | |
| 7,247,146 B2 | 7/2007 | Tonelli et al. | |
| 2004/0034317 A1 | 2/2004 | Gorsuch et al. | |
| 2004/0084358 A1 | 5/2004 | O'Mahony et al. | |
| 2004/0127840 A1 | 7/2004 | Gara et al. | |
| 2006/0084906 A1 | 4/2006 | Burbank et al. | |
| 2007/0278155 A1 | 12/2007 | Lo et al. | |
| 2010/0089806 A1 | 4/2010 | Peters et al. | |
| 2010/0094192 A1 | 4/2010 | Peters et al. | |
| 2010/0094194 A1 | 4/2010 | Peters et al. | |

OTHER PUBLICATIONS

Notice of Allowance mailed Oct. 4, 2012, for U.S. Appl. No. 12/577,513.
Notice of Allowance mailed Jan. 29, 2014, for U.S. Appl. No. 12/183,527.
Office Action mailed Jan. 11, 2012, for U.S. Appl. No. 12/183,527.
Office Action mailed Jun. 28, 2011, for U.S. Appl. No. 12/183,527.

* cited by examiner

MODULAR HEMOFILTRATION APPARATUS WITH REMOVABLE PANELS FOR MULTIPLE AND ALTERNATE BLOOD THERAPY

CROSS-REFERENCE TO RELATED APPLICATIONS

This application is a divisional of U.S. patent application Ser. No. 12/183,527 filed Jul. 31, 2008, which claims priority to U.S. Provisional Patent Application No. 60/953,577 filed Aug. 2, 2007, the contents of these applications being incorporated by reference herein.

BACKGROUND OF THE INVENTION

Hemodialysis systems have been designed to carry out blood therapy procedures such as slow continuous ultrafiltration (SCUF), continuous veno-venous hemofiltration (CVVH), continuous veno-venous hemodialysis (CVVHD) or continuous veno-venous hemodiafiltration (CVVHDF). These therapies, referred to as CRRT, are designed for removal of metabolic waste and excess fluid from patients in fluid overload and who need renal support. Presently available extracorporeal blood treatment apparatus often requires inconvenient and time consuming setup procedures including cleaning and/or replacing the blood and/or fluid tubing for different patients and for different therapies. Such procedures may require the apparatus to be removed from a patient's bedside or room to another location, or replacing an apparatus with a system that is set up and configured for carrying out a specific therapy.

U.S. Pat. No. 5,910,252 describes an apparatus configured for performing the different blood therapies and provides means for selecting one of the therapies to be carried out. The described apparatus is an assembly of all pumps, tubing, multiple fluid supply reservoirs, waste fluid container and filter cartridge necessary for performing any one of the selected blood therapies.

U.S. Pat. No. 6,200,485 describes another multipurpose hemofiltration system comprising an assembly of a blood filter cartridge, pumps, fluid reservoir and waste fluid container, components for comparing the weights of the fluid reservoir and waste fluid container and means for controlling the pump operations and rate in response to the compared weights during the therapy.

A Prismaflex™ system marketed by Gambro of Lakewood, Colo. offers selection of different CRRT therapies. The system allows the user to select a prepackaged, preassembled assembly incorporating all of the components including specific column and type of filter membrane or membrane filter surface area and all preconnected tubing for carrying out the selected therapy.

SUMMARY OF THE INVENTION

The apparatus and system described herein provides a flexible treatment platform for performing several different therapies for separating and removing undesirable components from blood as well as plasma separation and plasma treatment including plasmapheresis and therapeutic apheresis. The basic apparatus is a lightweight, portable, modular assembly including a housing having a plurality of peristaltic pumps secured in the housing together with a computer/controller. Manually removable and replaceable panels are provided with tubing sets mounted on the panels and configured for easy installation and replacement on the modular housing. The tubing kits on each of the different panels are configured and formed to readily engage one or more of the peristaltic pumps and for being connected to or disconnected from a filter cartridge, fluid supply bags and waste bags. The system provides a method allowing the physician or therapist to select a therapy, manually install a selected fluid control panel and selected filter cartridge, and thereafter, if desired, quickly and efficiently change the therapy by manually exchanging a panel and/or filter, or replacing a clogged filter. Such features as well as others, methods, advantages and operations of the apparatus will be disclosed in the following Detailed Description.

DETAILED DESCRIPTION OF THE PREFERRED EMBODIMENTS

It is understood that different patients have different medical conditions that require a selected therapy, or multiple or alternating therapies, Such different therapies may also call for use of different filter cartridges or columns as well as different tubing routing and setups. Moreover, there may be a need to exchange filter cartridges or columns during a procedure if the cartridge has failed or has become clogged.

The apparatus described herein is designed for convenient setup to provide CRRT selection as well as plasma separation, plasma exchange (TPE) and plasma treatment, such as therapeutic apheresis (TA), and thereafter, if desired, efficiently and economically modify the apparatus configuration to carry out a different blood therapy or plasma treatment. A blood tubing panel and fluid tubing panels are provided with identification components which are sensed or read by the computer/controller capable of reading and identifying which tubing panel and filter column are installed and for displaying that information to inform a physician or therapist that the installed filter column and blood and fluid panels are capable of performing the desired therapy. When a different therapy is desired at any time, or if a filter column needs to be replaced for any reason, by simply disconnecting the tubing ends and/or the filter, and replacing the filter or a panel, the apparatus configuration change can be readily made without the necessity of removing the blood access and blood return devices from the patient and minimizing interruption of the therapy. For example, to treat acute congestive heart failure, the apparatus may be set up to initially remove only excess plasma water from the patient's blood by installing an ultrafilter cartridge and a fluid side panel configured to direct plasma water from the ultrafilter to a fluid waste bag. Following ultrafiltration, the apparatus may be modified to perform CVVH, CYVHD or CVVHDF on the same patient by switching filter cartridges, adding a saline supply reservoir and/or dialysate bag and, if desired, a plasma replacement fluid bag, and continuing the blood therapy with minimal interruption. Similarly, by simply replacing a hemofilter cartridge with a plasma separation cartridge and adding a plasma infusion bag, the apparatus is configured for plasma replacement therapy. Alternatively, the plasma may be treated by mounting therapeutic apheresis components.

Figure 1:
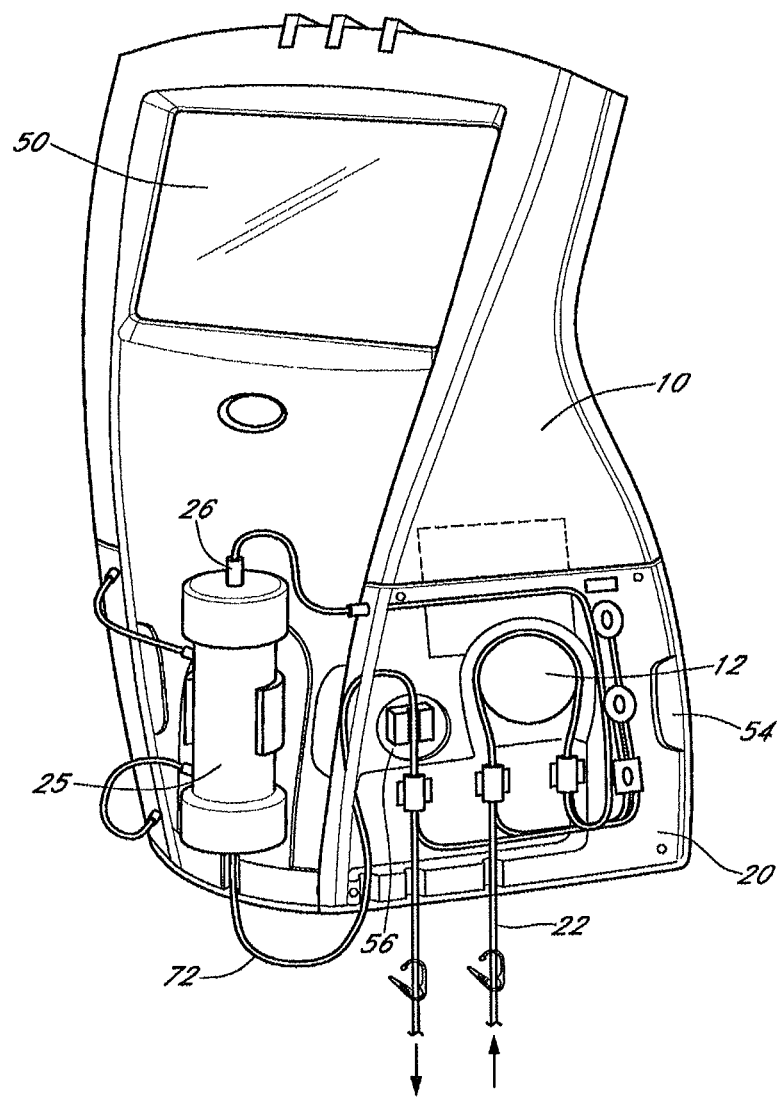
FIG. 1 illustrates one side and the front of the housing of the apparatus with a panel installed showing blood supply tubing engaging a blood pump.
Figure 2:
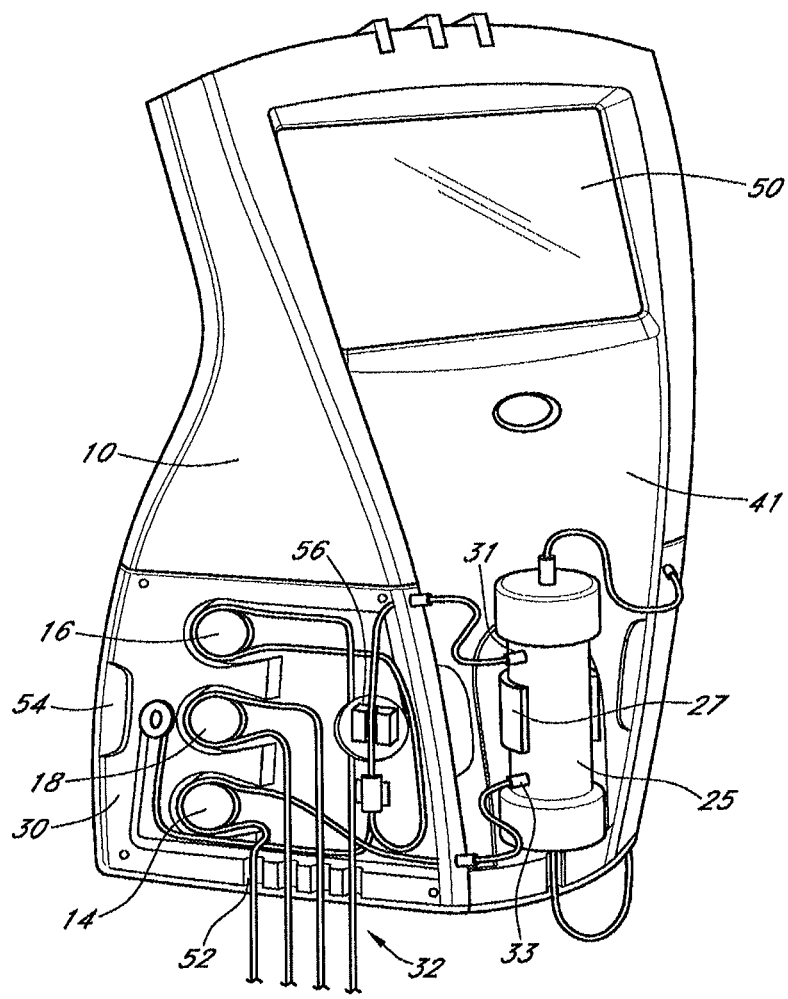
FIG. 2 illustrates another side of the housing assembly with a panel installed having fluid supply tubing engaging a plurality of peristaltic fluid pumps and connected to a filter cartridge.
Figure 3:
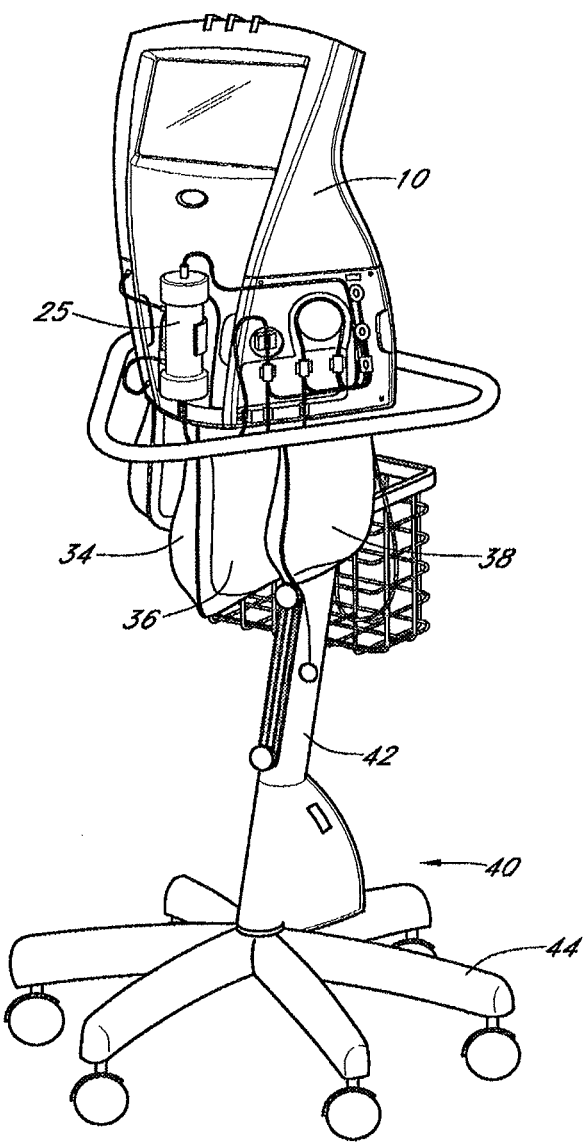
FIG. 3 illustrates the front and one side of the housing with a fluid supply bag and a collection bag mounted on a support pole and leg and caster assembly.

In FIGS. 1, 2 and 3 the housing assembly 10 is shown in which are secured the pumps, a computer/controller for operating the pumps and the system in carrying out the therapy, and to which housing the different removable and replaceable panels with mounted tubing are installed. In FIGS. 1 and 2, the front and sides of the housing assembly 10 are shown, the housing assembly including a screen 50 on which may be displayed information for guiding a user through operation of the system as well as notification of pump rates, alarms, and instructions on proceeding through operation of the blood therapy treatment, Preferably the screen is a touch screen provided with icons or other displays whereby the operation interacts with the computer by touching the screen to transmit the desired commands, instructions, or information. FIG. 1 shows the "blood side" of the housing assembly with manually mounted, removable and replaceable panel 20. Each panel is shaped to be easily manually installed and removed from an opening or cavity at the side of the housing. A panel preferably comprises a synthetic resin such as polycarbonate or other plastic and may be transparent or translucent to allow observation of the tubing on the inside of the installed panel. The blood side of the housing assembly includes a peristaltic blood pump 12 and blood tubing 22 mounted on the inside of the panel configured and shaped to engage a rotor of pump 12 when the panel is installed as shown.

FIG. 2 shows the "fluid side" of the housing assembly with panel 30 and fluid tubing 32. The fluid tubing is mounted on the inside of the panel and is configured and shaped to engage a plurality of different fluid pumps secured on the inside of the housing assembly. In the embodiment of FIG. 2, three peristaltic fluid pumps 14, 16 and 18 are shown with the fluid tubing 32 engaging the pumps with the panel 30 installed. Like panel 20 on the blood side of the housing assembly, panel 30 is similarly shaped for easy installation or removal from the housing assembly. As shown in FIGS. 1 and 2, the panels 20 and 30 include appropriate notches or recesses 52 to provide a pass-through for the tubing into and out of the housing. A handle recess 54 may be provided to allow an operator to grasp a panel during installation and removal. The various recesses and notches may be formed on the panels and/or the housing. Other openings such as holes or ports 56 are provided on the panel to allow observation and access to components positioned along the tubing such as air detectors and blood detectors. The tubing is conveniently secured on the interior or inside surface of each respective panel. For example, the tubing may be secured in slots, recesses or channels formed on the inside panel wall. Clips, brackets, hangers, etc. may also be used for securing the tubing. The tubing may also be secured by using any suitable adhesive, a UV curable adhesive or an ultrasonic weld between the panel wall and tubing that has been configured and shaped as desired.

Figure 7:
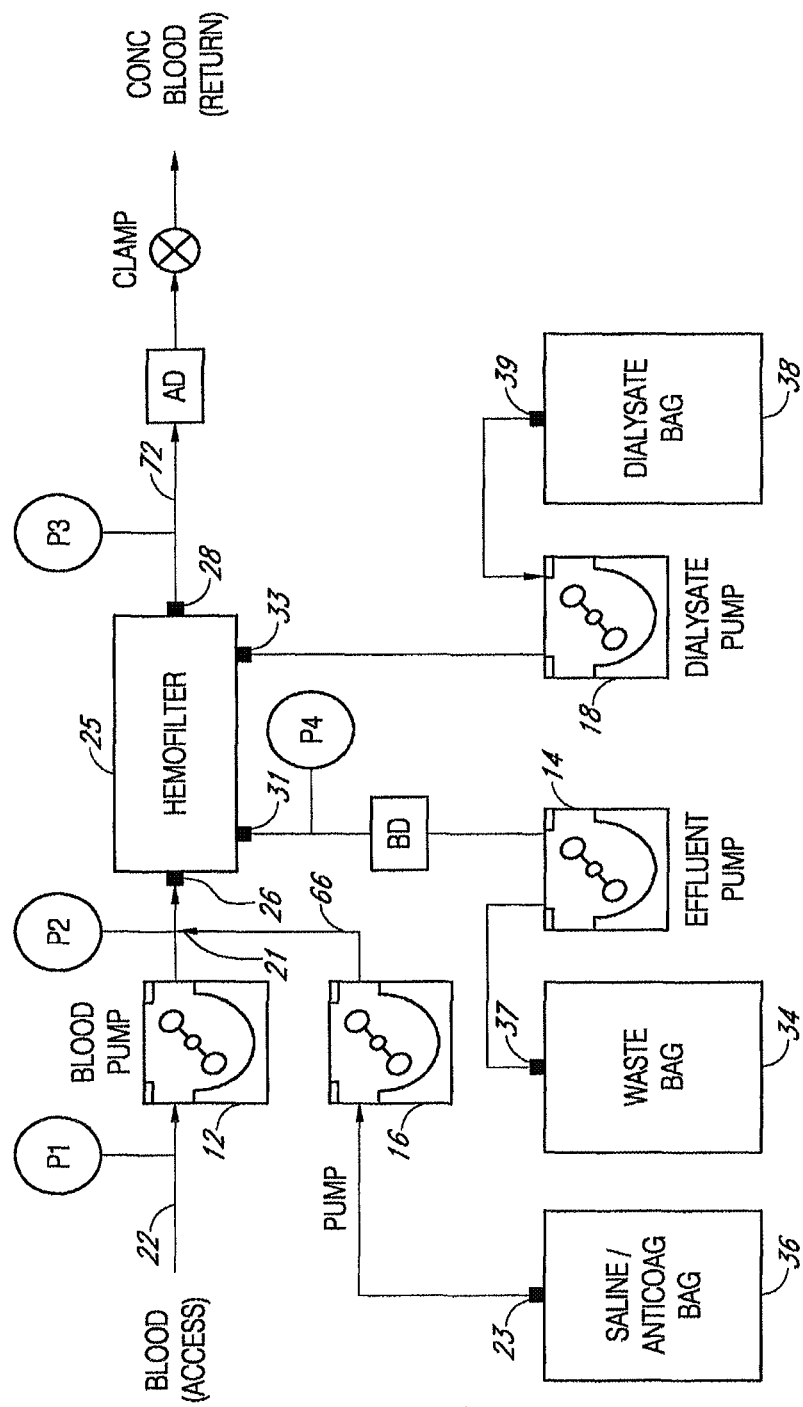
Figure 8:
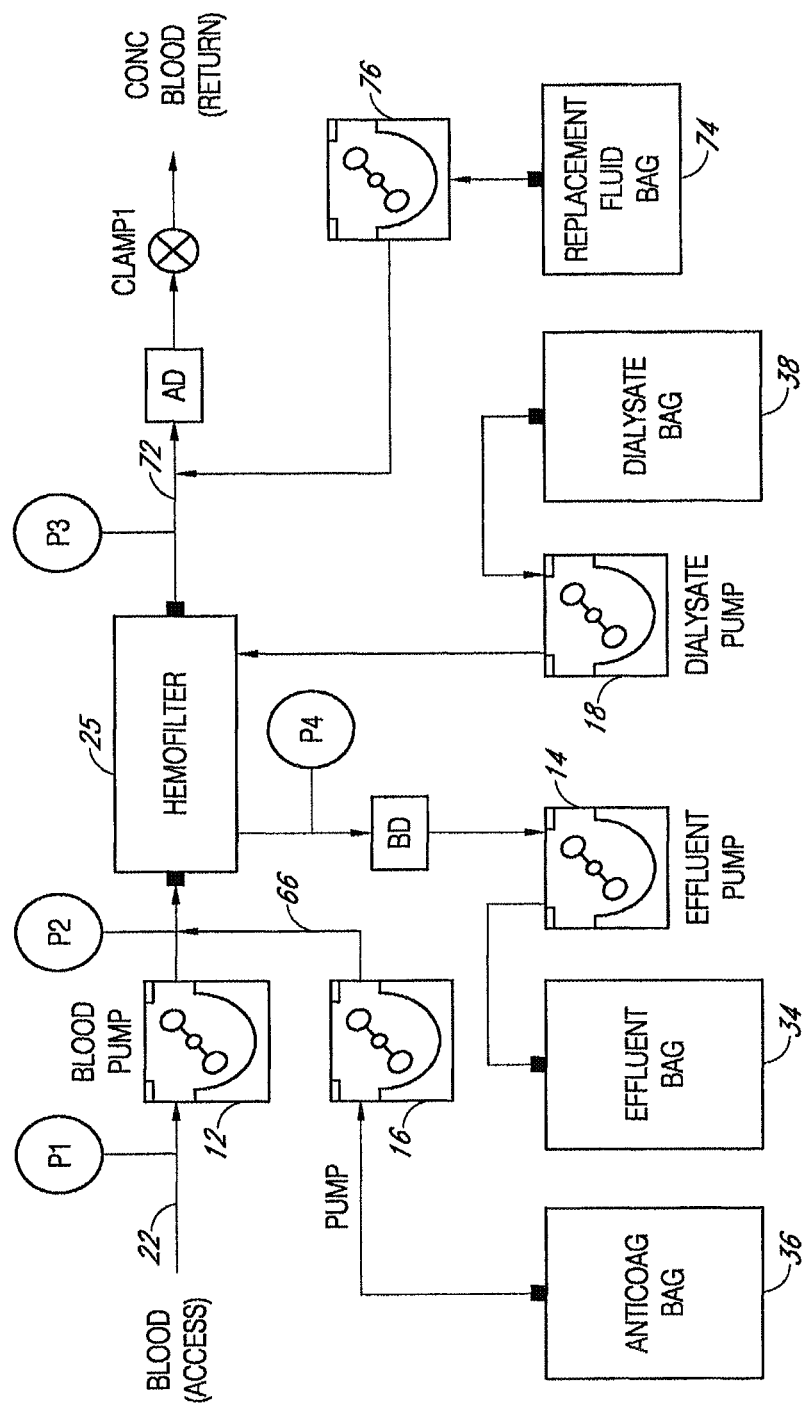
Figure 9:
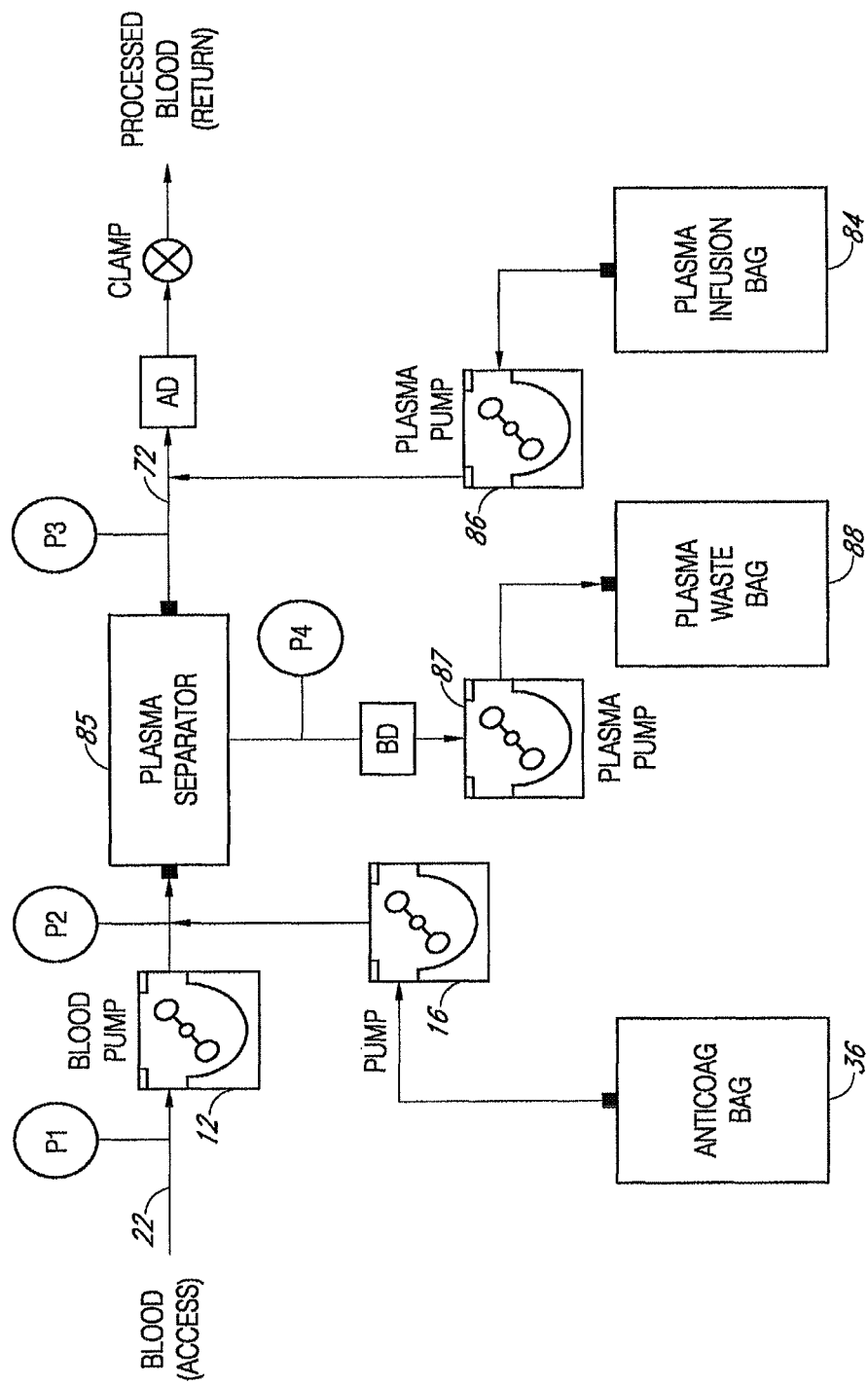
FIGS. 9 and 10 schematically illustrate plasma separation and plasma treatment apparatus embodiments.

FIG. 3 illustrates a preferred embodiment of the blood treatment apparatus which includes containers or bags 34, 36 and 38 for use in the treatment embodiments described and illustrated in FIGS. 7, 8 and 9. The apparatus includes a support column 42 as well as base 40 with legs 44 and casters.

Figure 4:
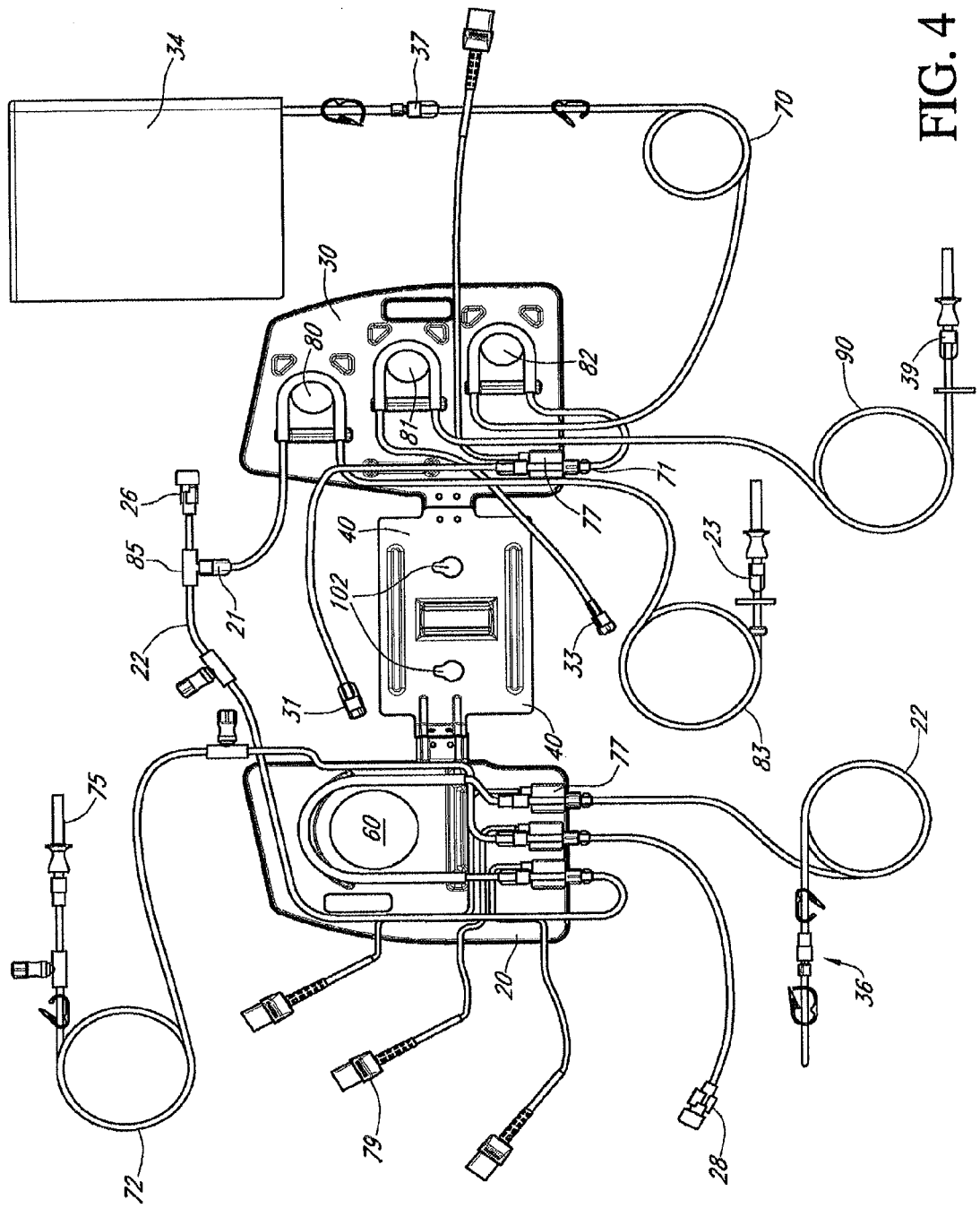
FIGS. 4 and 5 are drawings showing inside and outside views, respectively of a panel assembly and component configurations.
Figure 5:
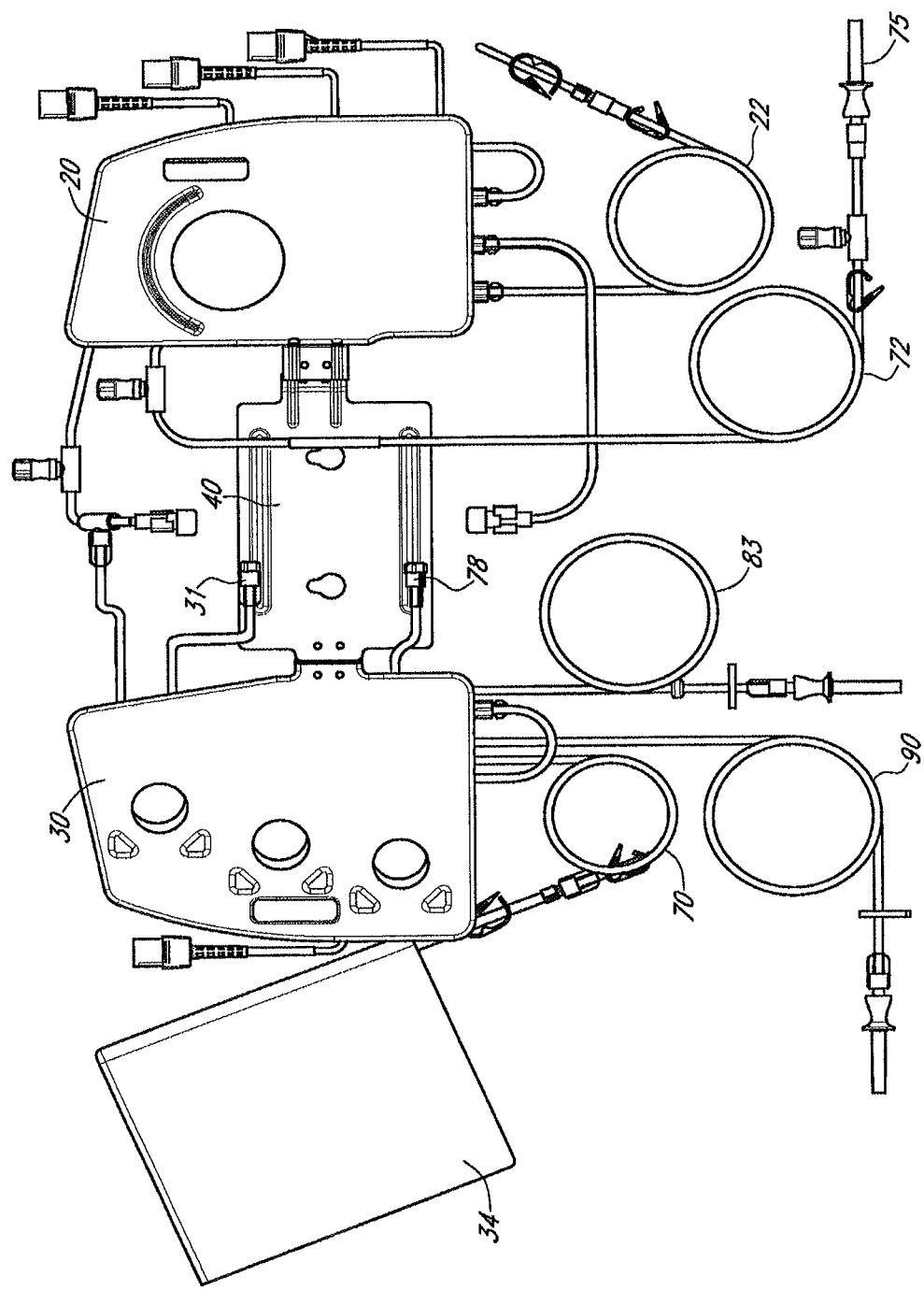

FIGS. 4 and 5 show inside and outside views, respectively, of preferred panel assembly embodiments. Panel 20 is the blood side panel having a large opening or port 60 for receiving a blood pump. Blood supply tubing 22 is looped around port 60 to cooperate with a rotor pump to pump blood from a patient to a filter column (not shown) to be connected to the tubing by connector 26. Blood return tubing 72 is provided with a connector 28 at one end for connecting to a filter column outlet port and a needle cannula assembly 75 at the opposite end for returning treated blood to a patient. Three pressure transducers 77 and transducer plugs 79 are also provided as are various tubing clamps. The apparatus will also include volume sensors, pressure sensors, blood leak detectors and air detectors connected along the tubing.

Fluid side panel 30 includes three fluid pump ports 80, 81 and 82 with tubing loops around each port for cooperating with the different fluid pumps. Effluent tubing 70 is provided with a connector 31 at one end for being connected to an effluent outlet on a filter column and a connector 37 at the opposite end for connection to a waste bag 34, which is an optional component of the panel assembly. A pressure transducer 71 is used along the effluent tubing. Tubing 83 will supply saline or replacement fluid from a bag or container. The saline may also contain an anticoagulant, and is pumped via a fluid supply pump at port 80 to a T connector 85 joining tubing 83 with blood supply tubing 22 downstream from a filter column (not shown). In the embodiment shown, a dialysate fluid supply tubing 90 is provided for supplying dialysate fluid to a hemofilter also configured for removing metabolic waste via diffusion as shown in FIG. 6 and as will be discussed hereinafter. Connector 33 at one end of the dialysate fluid tubing will be connected to a filter column. If only excess plasma water is to be removed from blood via simple ultrafiltration as described and shown in FIG. 5, the fluid panel may be configured without providing dialysate fluid tubing and even formed without a port for receiving a dialysate pump. However, in the process of molding a fluid panel, it is preferred to form a blank panel provided with three fluid pump ports and secure fluid tubing in the desired different configurations for different treatment options. A second optional bag is also shown which may be used as a priming waste bag. Bags for supplying replacement fluid such as saline, albumen or plasma, or for supplying dialysate fluid are normally supplied by the hospital, clinic, or treatment center. The bags are optional and may not be part of the panel assembly.

A third blank panel 40 is also shown on which a filter cartridge or column will be secured. A specific cartridge capable of carrying out a specific set of blood therapies may be mounted on the panel which is provided with a recess for receiving the cartridge and may also include clips, clamps, brackets or other components such as tape or a Velcro strap for securing a selected filter cartridge. Identification, e.g., bar code, may be on the filter cartridge, to be read by the computer to identify the type of cartridge and/or the procedures for which the cartridge is capable. The panels may be connected, for example, using hinges or flexible connectors or brackets as shown, or may be separated. A connected panel set allows the operator to mount the panel assembly components in a single operation, and also install and exchange selected filter cartridges on the blank center panel, as desired. The side panels may be provided with slots for receiving hangers, posts, brackets, clamps or other panel support members extending from the housing for mounting and supporting the panels. Front panel is provided with slots 102 for receiving mounting posts.

An alternative to the use of a third removable panel as described above on which a filter cartridge may be permanently or removably secured, the housing may be designed as illustrated in FIG. 2 whereby the front cover 41 of the housing is formed to provide a slot, recess or bracket 27 into which a filter cartridge 25 may be removably installed. The front cover of the housing may be also provided with clips, clamps or brackets for holding the removable cartridge in place in the recess, or an interchangeable bracket or tape or Velcro strap may be supplied for such a purpose. In such an embodiment, the front cover of the housing is also preferably provided with an opening or port through which computer sensible filter cartridge identification can be scanned or otherwise read or identified from within the housing. Alternatively, a filter cartridge identification scanning component may be installed on the front cover of the housing.

The tubing mounted in each of the respective blood and fluid panels are also provided with components for easily, quickly and efficiently connecting and disconnecting the tubing to other components of the apparatus. The ends of the different tubing sets are provided with manually operated connector devices such as connectors 31 and 37 at the ends of effluent fluid tubing 70 for being connected to a hemofilter and waste bag 34, connectors 21 and 23 for connecting the ends of saline fluid tubing 83 to a saline bag (not shown), and blood tubing 22 and connectors 26 and 28 for connecting the blood fluid tubing 22 and 72 to hemofilter 25 (FIG. 1). Needle and catheter assembly components 36 and 75 at the ends of the blood tubing 22 for patient blood access and patient blood return tubing 72 are shown. Connector 33 connects dialysate fluid tubing 90 to the hemofilter and connector 39 to a dialysate bag (not shown). Examples of such connectors include clips, clamps, threaded and quick-disconnect connectors and other releasable fittings allowing a therapist or physician to easily, manually, efficiently and selectively change filters as well as tubing panels, as required or desired.

Figure 6A:
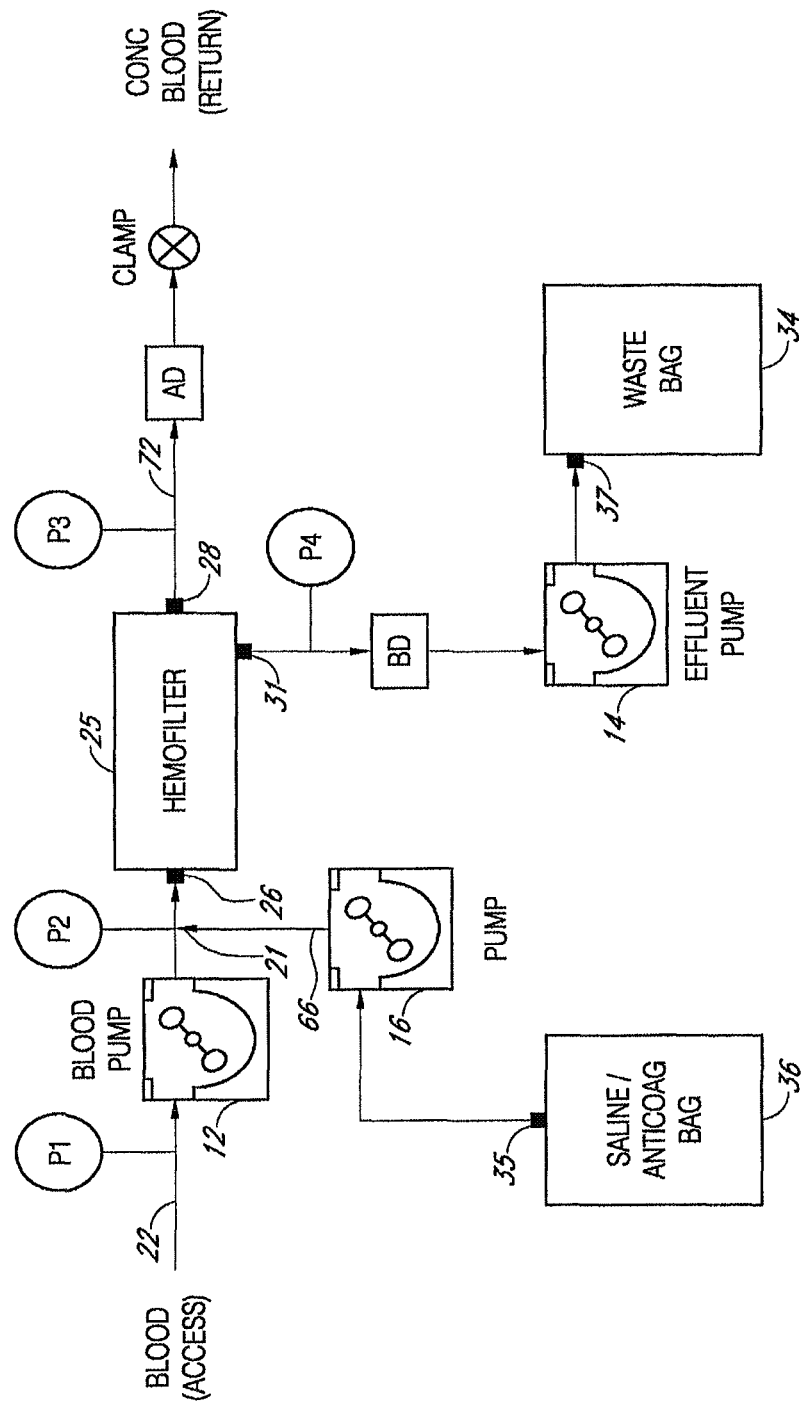
FIGS. 6A, 6B, 7 and 8 schematically show components of the apparatus configured for carrying out selected blood filtration therapies.

FIGS. 6A, 7 and 8 schematically illustrate different blood therapies and treatments which may be carried out using different panel and tubing sets and different hemofilter columns as described above. For removing plasma water in a single stage, the hemofilter selected may be an ultrafilter cartridge, the blood panel and tubing connected between a patient blood access and return and to the ultrafilter. The fluid tubing panel is configured to engage effluent pump 14 to direct plasma water from the ultrafilter to the waste bag, and to pump 16 for directing saline from a bag 36 to blood tubing 22 upstream from the ultrafilter to dilute the blood prior to ultrafiltration. Alternatively, the saline fluid tubing may be connected to the ultrafilter. It may be desirable also to add an anticoagulant such as heparin, a citrate, or other known anticoagulant to the saline fluid. Blood pump 12 pump blood through the blood tubing 22 from the patient to the ultrafilter and then to a patient return device.

FIG. 7 illustrates operation of an apparatus embodiment in which the hemofilter is configured to remove metabolic waste via diffusion as well as excess fluid or plasma water via convection. The system pumps blood through the hemofilter cartridge and dialysate at counter flow to the blood outside of the filtration membrane. The system pumps the dialysate and excess fluid into a waste bag and concentrated blood is returned to the patient. Thus, in addition to the components illustrated in FIG. 6A, the fluid tubing panel includes tubing configured to engage dialysate pump 18 which directs the dialysate from bag 38 to the hemofilter. Such combination of hemofilter and fluid and blood panels allows the apparatus to operate to perform hemodialysis or hemodiafiltration.

The apparatus configuration shown in FIGS. 6A and 7 and described above may be modified to direct saline or replacement fluid into the patient blood return line downstream from the hemofilter. Thus, instead of pumping fluid from bag 36 to blood supply tubing 22 upstream from filter 25, the saline supply tubing may be configured to direct the saline, replacement fluid, plasma and/or albumin to the filtered blood being returned to the patient. Typical commercially available replacement fluids contain electrolytes such as chloride salts of calcium, magnesium, potassium and sodium, sodium bicarbonate, proteins and other nutrients such as lactic acid and dextrose. The selection of suitable replacement fluids and their use are well known to those skilled in the art. Such an embodiment may be provided by installing an additional length of tubing (not shown) between fluid tubing section 66 and blood tubing 72. Pinch clamps (not shown) may be installed along the added tubing and tubing section 66 to allow an operator to close either of the saline supply tubes thereby selectively directing the saline or replacement fluid upstream and/or downstream from the hemofilter. Other alternative components such as a valve at the junction of the added tubing with tubing section 66 may be used.

An alternative system embodiment using five pumps is illustrated in FIG. 8. Anticoagulant is introduced upstream from the hemofilter and replacement fluid is added downstream from the hemofilter. In the system shown, a small amount or bolus of anticoagulant may be periodically supplied to the blood stream in amounts sufficient for regional effect to prevent or reduce clotting along the blood inlet tubing and at the filter membrane. Anticoagulant pump 16 cooperates with fluid supply tubing 66 which may be connected to blood supply tubing 22 or directly attached to the hemofilter. Replacement fluid is pumped from replacement fluid bag 74 to blood supply tubing 72 by pump 76.

Figure 6B:
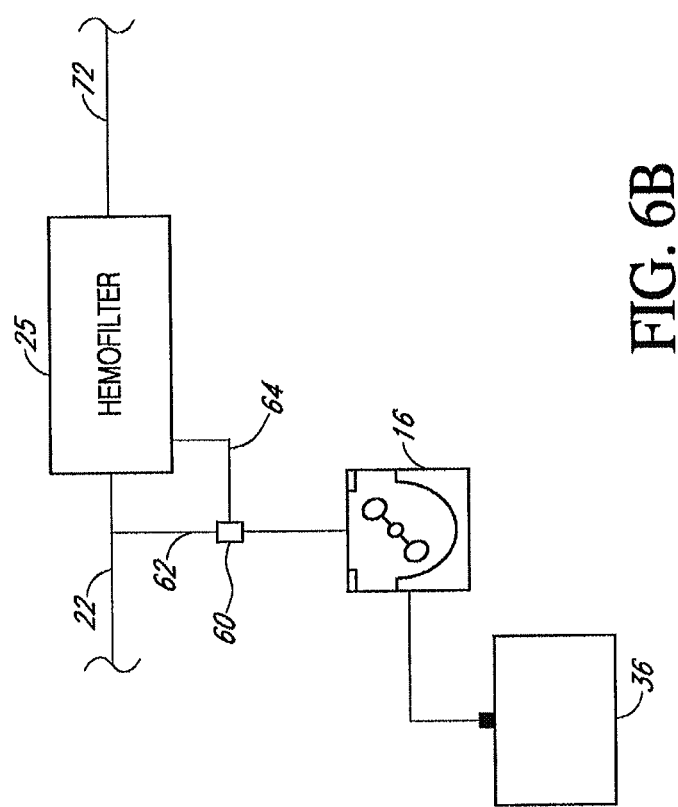

The apparatus may also be configured to accomplish a backflush of an ultrafilter membrane. The backflush may be accomplished on a selected or periodic backflush cycle, or it may be accomplished in response to detection of transmembrane pressure of the filter cartridge or other sensing of clogging of the membrane pores. For example, the system may include one or more pressure transducers for monitoring pressure of the plasma waste fluid as an indication of when the filter pores are becoming clogged to an extent necessary to terminate the wastewater extraction and initiate backflushing. FIG. 6B illustrates schematically a portion of the apparatus of FIG. 6A which is modified by incorporating a selectively operated valve 60 in the fluid line which directs saline from the saline bag 36 to the hemofilter or ultrafilter 25. Such an apparatus embodiment may be operated to initiate backflush by temporarily terminating the pumping of blood to the filter cartridge 25 via blood tubing 22 and operating valve 60 so as to temporarily stop the flow of the saline to blood tubing 22 via fluid tubing section 62 and instead directing the saline fluid into the filter cartridge on the outside of the filter membrane. The bolus of a backflush fluid will be of a volume and duration sufficient to perform the desired backflush, after which valve 60 is again operated to direct the flow of the saline to blood tubing 22 and the blood pump again operated to begin blood therapy procedures. Other details for such a backflushing may be understood by referring to U.S. Pat. No. 6,659,973, the description of which is incorporated herein by reference in its entirety. Again, the backflush procedure and embodiment is optional.

The multiple panel assembly may also be used for carrying out plasma separation, plasmapheresis, plasma exchange, liver support and therapeutic apheresis. Such plasma separation and treatment configuration will utilize similar configurations as described and shown in the figures previously discussed. However, the hemofilter or ultrafilter will be replaced by a plasma separation cartridge in which plasma is separated from whole blood from the patient. The recovered plasma is thereafter discarded and replaced, or the plasma I treated for separation and removal and/or neutralization of selected disease-related components or other substances such as poisons, toxins or drugs, etc. In FIG. 9, the system illustrated is configured to carryout plasma replacement. Plasma from a patient is pumped to a plasma separation cartridge 85 where plasma is separated across the cartridge membrane or membranes and pumped by a plasma pump 87 to plasma waste bag 88, Replacement plasma from plasma infusion bag 84 is pumped with a third fluid pump, second plasma pump 86, to the patient blood return tubing 72. An anticoagulant source and pump are also shown and which components are operated and function as previously described. One fluid pump will pump anticoagulant to the blood supply tubing 22 upstream from a plasma separation cartridge and a second fluid pump will direct separated plasma to a plasma waste bag.

Figure 10:
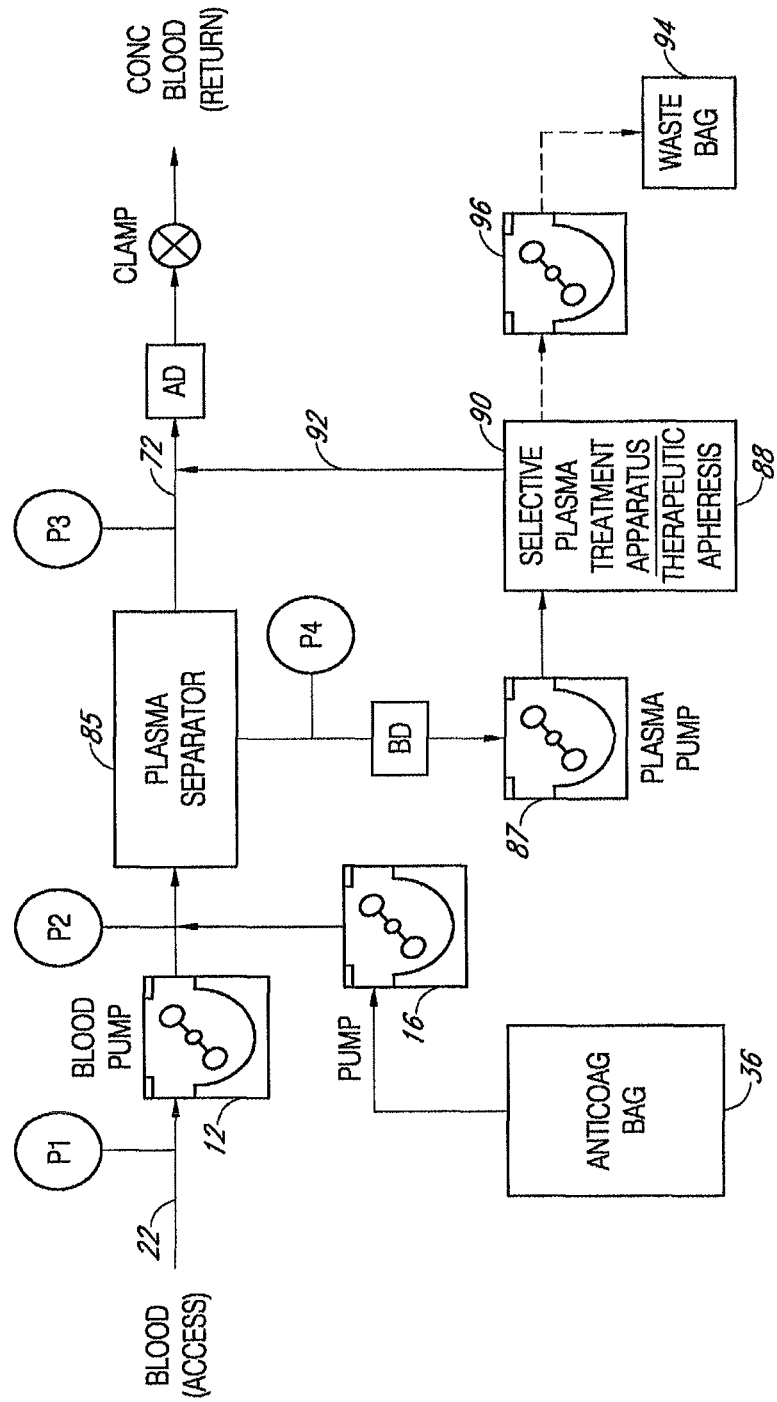

FIG. 10 illustrates an embodiment of the apparatus for processing separated plasma for selective plasma treatment. Such selective plasma treatment is referred to as therapeutic apheresis, and includes apparatus capable of selectively removing disease-related components such as toxins, antibodies, proteins, pathogens including bacteria, virus, etc. as well as removing or neutralizing drugs, poisons, or other selected chemical substances. As shown in FIG. 10, a selective plasma treatment apparatus or therapeutic apheresis apparatus 90 is supplied with separated plasma via plasma pump 87 for treating the plasma. Such selective treatment apparatus may include plasma exchange components, centrifugal or membrane-separation filters, cascade or multiple filtration membranes and columns, one or more absorption cartridges capable of absorbing specific disease-related components or drugs, and activated charcoal cartridges. Other examples of such selective component removal apparatus includes specialized columns incorporating compositions such as cross-linked polyvinyl alcohol gel beads or microporous cellulose beads for removing specific amino acid ligands and antibodies. Other examples are components capable of chemically processing the plasma to precipitate heparin, salt-amino acids, or for effectively neutralizing drugs, poisons or disease-related components in the plasma. Such apparatus may be used for liver support functions as well. Moreover, the selective plasma treatment apparatus may combine different plasma treatment components used in series or parallel for simultaneously or concurrently carrying out multiple plasma treatment or therapy where such need is indicated. The treated plasma is directed to the patient via tubing 92 connected to patient blood return line 72. If needed, a separate fourth fluid pump may be used for pumping the treated plasma to the patient return line or to an effluent container. In FIG. 10, a supplemental fluid pump 96 is also shown for directing waste fluid from the selective plasma treatment apparatus 90 to a waste bag 94. Such an optional effluent or waste fluid component may be used where the selective plasma treatment apparatus 90 separates plasma components from the plasma which are to be discarded. Additional description of selective component removal apparatus and technologies are described in U.S. Pat. No. 6,849,183, the relevant portions thereof which are incorporated herein by reference, as well as in Therapeutic Apheresis, Vol. 1, No. 2, May 1997, pages 135-146. Other examples of such cartridges or plasma exchange components, filters, etc. are disclosed in U.S. Pat. No. 5,605,627, the relevant portions of which are incorporated herein by reference. The selective plasma treatment apparatus may be designed to allow an operator to exchange, replace or modify the configuration of the filters, columns, cartridges, etc. in order to accomplish different plasma treatments on a patient, if desired.

The systems described hereinabove allows the physician or therapist the flexibility of selecting and mixing and matching different hemofilter, plasma replacement or plasma treatment columns with different fluid tubing set configurations for any selected CRRT therapy and/or plasma separation and plasma treatment using the same blood tubing set. Thus, the apparatus can be modified to perform different, alternate therapies on a single patient without disturbing the blood tubing connections as well as to efficiently and economically reconfigure the system for different patients.

What is claimed is:

1. A modular panel assembly comprising:
   an apparatus housing having a plurality of cavities configured to accommodate manual installation and removal of modular panels on and from the housing, respectively;
   a modular first panel configured to be installed and removed on and from the apparatus housing independent of any other panel, comprising a generally flat, planar panel configured to be manually installed on the apparatus housing, said modular first panel having blood supply tubing mounted thereon, said blood supply tubing comprising first blood tubing configured to engage a peristaltic blood pump and having connectors configured to releasably connect a first end thereof to a device for directing blood from a patient and to releasably connect a second end thereof to, an inlet of a blood filtering cartridge or plasma separation cartridge and second blood tubing and having connectors configured to releasably connect a first end thereof to an outlet of a blood filtering cartridge or plasma separation cartridge and releasably connect a second end thereof to a device for returning blood to a patient; and
   a modular second panel, separate from the modular first panel and configured to be installed and removed on and from the apparatus housing independently of the modular first panel and any other panel, comprising a generally flat, planar panel configured to be manually installed on the apparatus housing, said modular second panel having fluid supply tubing mounted thereon comprising first fluid tubing configured to engage a peristaltic fluid pump and having connectors configured to releasably connect a first end thereof to an outlet of a blood filter cartridge or a plasma separation cartridge to releasably connect a second end thereof to a fluid collection container or to therapeutic apheresis apparatus, and second fluid tubing configured to engage a peristaltic fluid pump and having connectors configured to releasably connect a first end thereof to said first blood tubing or to an inlet of a blood filter cartridge and to connect a second end thereof to, a fluid supply container.

2. The modular panel assembly of claim 1 wherein said fluid supply tubing further comprises third fluid tubing configured to engage a peristaltic fluid pump and having connectors configured to releasably connect a first end thereof to a dialysate fluid supply container and releasably connect a second end thereof to a blood filter cartridge.

3. The modular panel assembly of claim 2 wherein said fluid supply tubing further comprises fourth fluid tubing configured to engage a peristaltic fluid pump and having connectors configured to releasably connect a first end thereof to a replacement fluid supply container or plasma supply container and releasably connect a second end thereof to said second blood supply tubing.

4. The modular panel assembly of claim 1 wherein said fluid supply tubing further comprises third fluid tubing configured to engage a peristaltic pump and having connectors configured to releasably connect a first end thereof to therapeutic apheresis apparatus and releasably connect a second end thereof to said second blood supply tubing.

5. The modular panel assembly of claim 1, further comprising: a modular third panel configured to be manually installed on an apparatus housing, said modular third panel having a blood filter cartridge or a plasma separation cartridge mounted thereon, and having a computer readable component identifying the type of filter cartridge.

6. The modular panel assembly of claim 1, further comprising: a modular third panel configured to be manually installed on an apparatus housing, said modular third panel including blood filter cartridge mounting components.

* * * * *